US007958794B2

(12) United States Patent
Sahibzada et al.

(10) Patent No.: US 7,958,794 B2
(45) Date of Patent: Jun. 14, 2011

(54) DEVICE FOR SENSING THE CONTENTS OF A FLUID IN A DUCT WITH A TUBULAR BODY EXTENDING INTO THE DUCT

(75) Inventors: Jörgen Sahibzada, Göteborg (SE); Per Olowson, Öckerö (SE)

(73) Assignee: Calectro AB, Vastra Frolunda (SE)

( * ) Notice: Subject to any disclaimer, the term of this patent is extended or adjusted under 35 U.S.C. 154(b) by 657 days.

(21) Appl. No.: 11/662,647

(22) PCT Filed: Jan. 5, 2006

(86) PCT No.: PCT/SE2006/000014
§ 371 (c)(1),
(2), (4) Date: Jun. 23, 2008

(87) PCT Pub. No.: WO2006/078205
PCT Pub. Date: Jul. 27, 2006

(65) Prior Publication Data
US 2008/0257011 A1 Oct. 23, 2008

(30) Foreign Application Priority Data
Jan. 24, 2005 (SE) ..................................... 0500175

(51) Int. Cl.
*G01D 21/00* (2006.01)
*G01N 7/00* (2006.01)
(52) U.S. Cl. ........................................ 73/866.5; 73/23.2
(58) Field of Classification Search .................... 73/864, 73/864.33, 863.41, 863.57, 863.51
See application file for complete search history.

(56) References Cited

U.S. PATENT DOCUMENTS

| 3,643,508 | A | * | 2/1972 | Schneider | 374/143 |
|---|---|---|---|---|---|
| 4,339,318 | A | | 7/1982 | Tanaka et al. | |
| 4,736,618 | A | * | 4/1988 | Usami et al. | 73/31.05 |
| 5,463,908 | A | | 11/1995 | Rosolia | |
| 5,773,726 | A | | 6/1998 | Mahoney et al. | |
| 6,015,533 | A | | 1/2000 | Young et al. | |
| 6,470,732 | B1 | | 10/2002 | Breton | |
| 2004/0050183 | A1 | | 3/2004 | Schimmoller et al. | |
| 2005/0160840 | A1 | | 7/2005 | Allmendinger | |

(Continued)

FOREIGN PATENT DOCUMENTS
DE 1533829 B1 8/1971
(Continued)

OTHER PUBLICATIONS
International Search Report (PCT/ISA/210).
(Continued)

*Primary Examiner* — Hezron Williams
*Assistant Examiner* — Nathaniel Kolb
(74) *Attorney, Agent, or Firm* — Harness, Dickey & Pierce, P.L.C.

(57) ABSTRACT

A device is disclosed for sensing the contents of a fluid flowing in a duct system, such as in a ventilation duct. In at least one embodiment of the invention, the device includes a sensing element and a tubular body extending over a cross-sectional portion of the duct at issue and a supply duct with an inlet facing the main flow direction of the fluid and a discharge duct with an outlet located downstream of the inlet, to divert from the flowing fluid a partial flow which is made to pass the sensing element and then re-enter the duct. The outlet is located upstream of the downstream boundary of the tubular body.

17 Claims, 3 Drawing Sheets

U.S. PATENT DOCUMENTS

2006/0027353 A1 * 2/2006 Luthi et al. .................. 165/11.1

FOREIGN PATENT DOCUMENTS

| DE | 29912622 U1 | 12/1999 |
| --- | --- | --- |
| DE | 20-2005-000060 | 4/2005 |
| EP | 0431345 | 3/1994 |
| EP | 0315175 | 1/1996 |
| EP | 0732568 | 9/2002 |
| EP | 1624295 A1 | 2/2006 |
| GB | 2347541 | 9/2000 |
| WO | WO0008452 A1 | 2/2000 |
| WO | WO 01/59737 | 8/2001 |

OTHER PUBLICATIONS

International Search Report dated Aug. 6, 2007, for European Patent Application No. 06700192.5-1234.

* cited by examiner

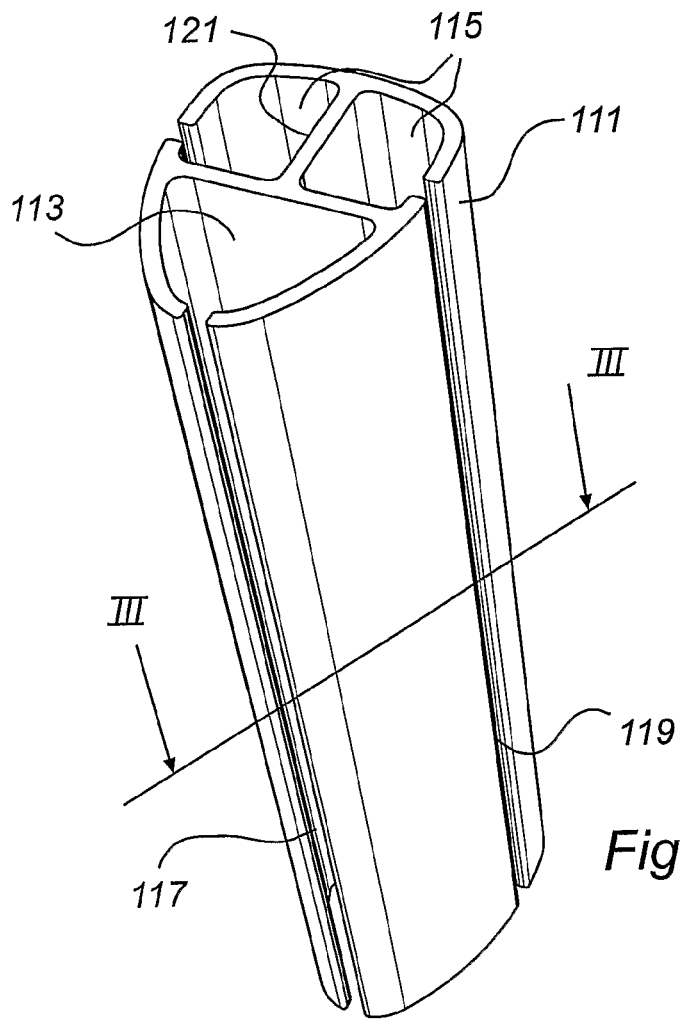
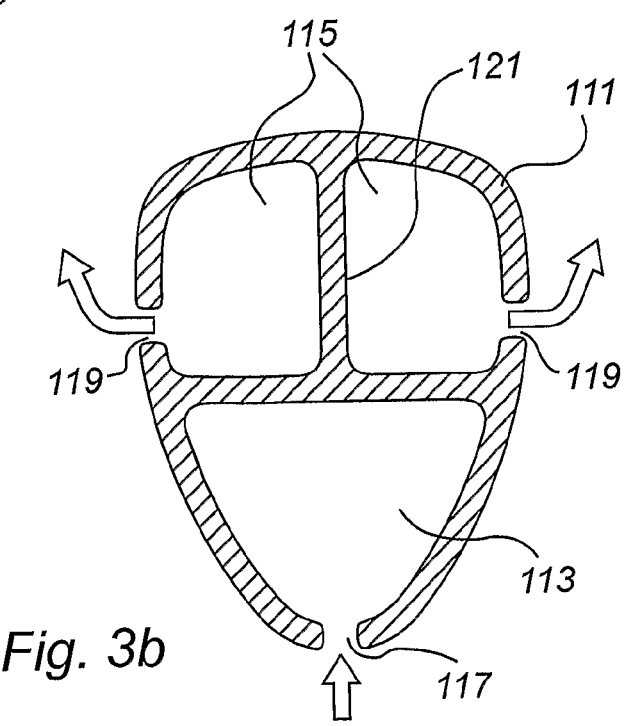

DEVICE FOR SENSING THE CONTENTS OF A FLUID IN A DUCT WITH A TUBULAR BODY EXTENDING INTO THE DUCT

FIELD OF THE INVENTION

The present invention relates to a device for sensing the contents of a fluid flowing in a duct system, such as in a ventilation duct, comprising a sensing element and a tubular body extending over a cross-sectional portion of the duct and having a supply duct with an inlet facing the main flow direction of the fluid and a discharge duct with an outlet located downstream of the inlet, to divert from the flowing fluid a partial flow which is made to pass said sensing element and then re-enter said duct.

BACKGROUND ART

When sensing, for instance, particles or gases in a fluid, such as a fluid in a ventilation duct, it is important for the sensing to be reliable. As a rule, such sensing is done by part of the fluid being made to pass a detector, such as a smoke detector, which is arranged outside the ventilation duct.

Different types of devices for such sensing are known, in which sensing occurs by fluid being diverted from the ventilation duct and being passed through a space past a detector in the same for sensing, after which the fluid is returned to the duct. If, for instance, a smoke detector senses that there is flue gas in the fluid from the ventilation duct, the smoke detector emits, for instance, a signal which can be connected to an alarm, or which can constitute an initiation signal to close the duct system etc.

These prior-art devices for sensing a fluid frequently have a not quite satisfactory function as regards safe and reliable registration of small amounts of, for instance, flue gas in said fluid. Therefore there is a need to improve the accuracy of such devices to detect the presence of gases and particles in small amounts in a fluid in, for instance, a ventilation duct.

SUMMARY OF THE INVENTION

An object of the present invention is to provide a device for sensing the contents of a flowing fluid, which at least partly satisfies the above need.

A further object of the present invention is to provide a device for sensing the contents of a flowing fluid, which device is configured so that a sufficient partial amount of fluid from the flowing fluid is allowed to pass the device for sensing and be returned to the flowing fluid.

The above objects and other objects that will be evident from the following description are achieved by a device for sensing the contents of a fluid flowing in a duct system, such as in a ventilation duct, according to claim 1. Preferred embodiments of the invention are defined in the dependent claims.

With the invention, it has been realised that by means of a tubular body with an inlet and outlet for diverting a partial amount of fluid that is to be sensed, it is possible to provide an increased throughput of the partial amount of diverted fluid compared with prior-art technique by arranging said inlet and said outlet in a certain relationship to the main flow direction of the fluid that is to be sensed.

According to one aspect of the invention, a device is provided for sensing the contents of a fluid flowing in a duct system, such as in a ventilation duct, comprising a sensing element and a tubular body extending over a cross-sectional portion of the duct at issue and having a supply duct with an inlet facing the main flow direction of the fluid and a discharge duct with an outlet located downstream of the inlet, to divert from the flowing fluid a partial flow which is made to pass said sensing element and then re-enter said duct, wherein said outlet is located upstream of the downstream boundary of the tubular body.

As a result, a sufficient partial amount of fluid in a main flow is allowed to be sensed by means of a sensing element by using a tubular body that has relatively small dimensions. It is desirable to keep the dimensions of the tubular body small so as to affect the main flow in the duct system as little as possible. The sufficient amount of diverted fluid to be sensed allows sensing that makes it possible to register the presence of particles and/or gases in the main flow which is to be sensed even in relatively small amounts. The registration of the presence of particles and/or gases in relatively small amounts in the main flow allows, in turn, sensing with good reliability and accuracy.

The realisation of the importance of the position of said inlet and outlet relative to the main flow direction of the fluid that is to be sensed is based on the fact that a desirable entraining effect through said tubular body and said housing arises owing to a pressure difference between the inlet and the outlet. The arrangement of said inlet and outlet relative to the main flow direction of the fluid that is to be sensed thus means that this pressure difference is affected, thus affecting the entraining effect. Consequently it is also possible to affect the partial amount of diverted fluid from the main flow.

In one embodiment of the invention, the tubular body is, in use, arranged to extend over the major part of the cross-section of the duct. In particular, it is convenient to arrange the tubular body so as to extend over essentially the entire cross-section of the duct.

By arranging the tubular body so as to extend over a substantial part of the cross-section of the duct, a partial amount of fluid can be diverted, consisting of a mixture of fluid taken from essentially the entire cross-section of the duct. By the diverted partial amount of fluid consisting of fluid transversely to a substantial part of the cross-section of the duct, it is increasingly ensured that gases and/or particles in local areas of the duct will not be left out to be registered.

Said outlet is preferably arranged upstream of a separation point, which separation point constitutes the area where the surface-parallel flow of the fluid relative to the outer surface of the tubular body essentially ceases. It has been found that the entraining effect through said tubular body and housing will be favourable by placing said outlet upstream of the separation point, whereby the amount of fluid that is allowed to flow through the housing reaches a favourable level.

Investigations and analyses have demonstrated that within an area upstream of said separation point there is an area where an essentially maximum speed of the flow that is surface-parallel to the tubular body occurs. It has also been found that a favourable entraining effect through the tubular body and the housing can be achieved by preferably placing said outlet so that the outlet is located in an area where said essentially maximum speed of the surface-parallel flow relative to the outer surface of the tubular body occurs.

The position of said essentially maximum speed is affected by the peripheral geometry of a section of the tubular body transversely to the longitudinal direction. Said area of the essentially maximum speed has, in one embodiment of said tubular body, been found to be located in the vicinity of an area where a tangent to the surface of the tubular body changes direction relative to the main flow direction of the fluid in the duct that is to be sensed. Thus, it has been found convenient to arrange the outlet so that it is located in an area where the peripheral lateral surfaces of the tubular body relative to each other, in a direction away from said inlet, change from a divergent extent to a convergent extent relative to the main flow direction of the fluid. In one embodiment of the invention, this constitutes the area where the section of the tubular body transversely to the longitudinal direction essentially has its maximum extent transversely to the main flow direction of the fluid. It has been found particularly convenient to place the outlet slightly upstream of said transition between the divergent extent and the convergent extent of the peripheral lateral surfaces of the tubular body.

In a preferred embodiment, at least one of the inlet and outlet consists of at least one elongate opening, for instance a slot. Such an elongate opening preferably has a width which is less than 5 mm, preferably 1-4 mm and in particular 2-3 mm. Moreover it is particularly convenient to arrange said elongate opening so as to extend along the major part of the portion of the tubular body which in use is positioned inside said duct. In an alternative embodiment, said elongate opening consists of a plurality of elongate openings, for instance two elongate openings, which are spaced from each other in the longitudinal direction of the tubular body.

By arranging at least the inlet as one or more elongate openings, it has been found that the diverted partial amount of fluid from the main flow of fluid in the duct advantageously consists of a relatively homogeneous mixture of fluid from essentially the entire extent of the elongate opening transversely to the duct. Since withdrawal of fluid for sensing from essentially the entire cross-section of the duct can be obtained in this manner, the risk decreases that only local areas of the fluid flowing in the duct are sensed in terms of identification of particles and/or gases. The possibility of such advantageous sensing of the main flow transversely to a substantial part of the cross-section of the duct makes it possible to register the presence of particles and/or gases with sufficient accuracy and reliability.

Furthermore it has been found that an advantageous relatively low pressure drop of the flow of the fluid through the tubular body and the housing can be obtained by designing the outlet so that it extends over a major part of the extent of the tubular body inside the duct. Similarly to the inlet, also the outlet is suitably arranged as one or more elongate openings. However, it should be noted that the outlet can be designed in alternative ways, where said relatively low pressure drop can be obtained, for instance as a plurality of spaced-apart holes or the like.

In a preferred embodiment of the device for sensing a flowing fluid in a duct system, a section of the tubular body transversely to the longitudinal direction preferably has a greater extent in the main flow direction of the fluid than transversely to the main flow direction of the fluid.

The device for sensing a flowing fluid in a duct system is advantageously provided with an outlet which consists of at least two opposite openings positioned on opposite sides of the tubular body relative to a plane which extends in the main flow direction of the fluid and through the longitudinal axis of the tubular body. By arranging the outlet as two opposite openings in this way, the above-described favourable entraining effect of fluid through the tubular body and the housing on both sides of the pipe is used, a suitable amount of fluid being allowed to be diverted from the duct system to be sensed and then be returned to the duct system. It is convenient for said discharge duct of the tubular body to consist of two duct portions which are spaced apart by a wall element, each duct portion being provided with an outlet.

BRIEF DESCRIPTION OF THE DRAWINGS

The invention will now be described in more detail with reference to the accompanying schematic drawings which by way of example illustrate currently preferred embodiments of the invention.

FIG. 3a is a perspective view of a portion of a tubular body of the device according to the invention shown in FIG. 2.

FIG. 3b is a cross-sectional view along line III-III of the tubular body according to the invention as shown in FIG. 3a.

DESCRIPTION OF PREFERRED EMBODIMENTS

The invention will now by way of example be described in more detail by means of embodiments and with reference to the accompanying drawings.

Figure 1A:
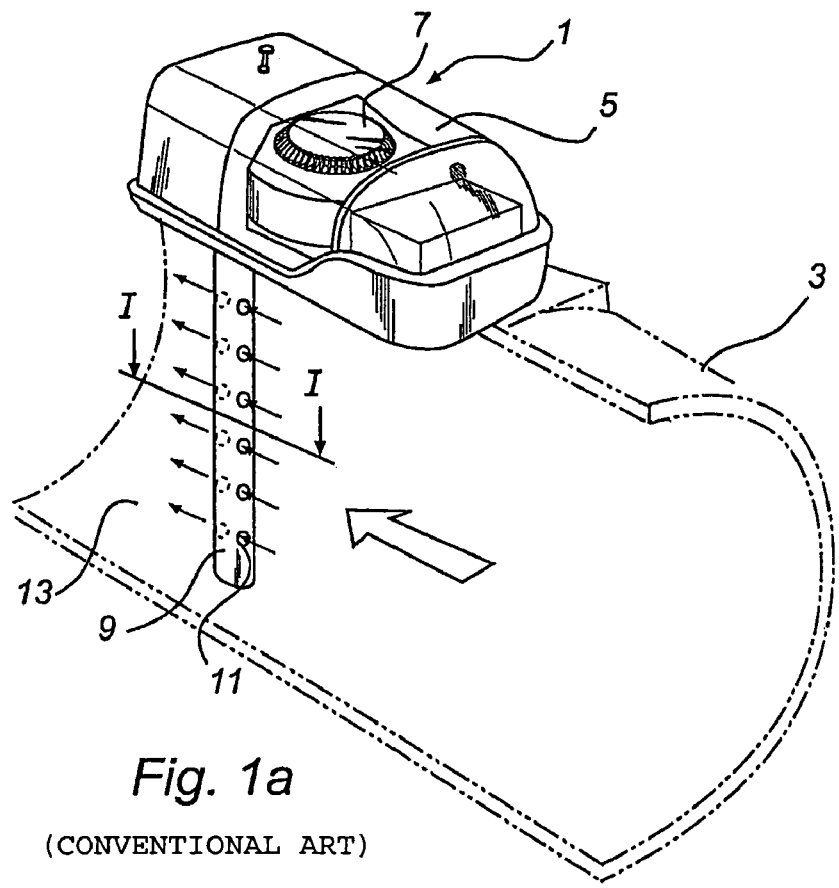
FIG. 1a schematically illustrates, partly in cross-section, a device according to prior art for sensing the contents of a fluid which flows in a duct system, such as in a ventilation duct.

FIG. 1a is a perspective view of a device 1 according to prior art for sensing the contents of a fluid flowing in a duct system 3, such as in a ventilation duct. Said device 1 according to prior art consists of a housing 5 which is adapted to accommodate a sensing element 7, which is provided with a throughput portion for supply and discharge of the fluid that is to be sensed. Moreover said housing 5 is adapted to be arranged on the outside of the duct system 3 and the fluid that is to be sensed is supplied to and discharged from said housing by means of a two-duct pipe 9, in which a first duct constitutes a supply duct and a second duct constitutes a discharge duct.

Figure 1B:
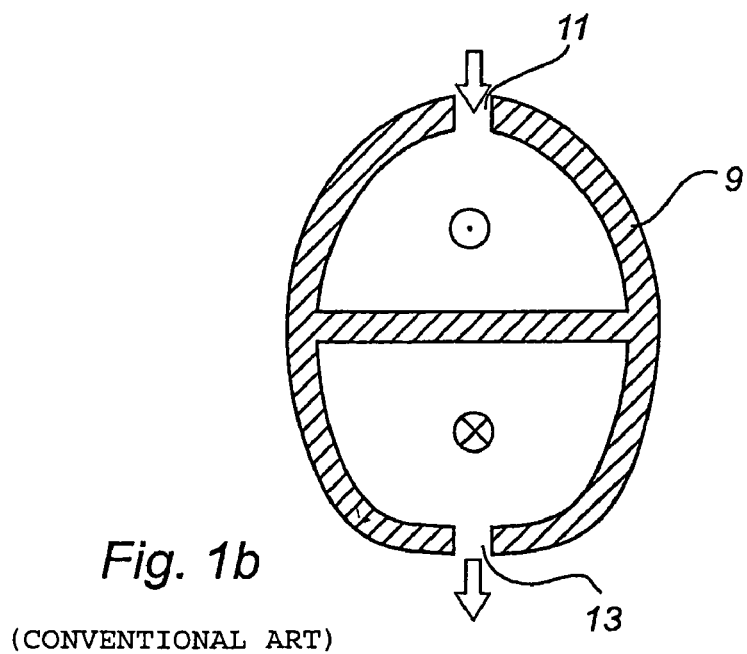
FIG. 1b is a cross-sectional view along line I-I of a tubular body of the prior-art device shown in FIG. 1.

The two-duct pipe 9 which is shown in cross-section in FIG. 1b is provided with an inlet 11 which is in fluid communication with said supply duct, which inlet 11 is formed as a plurality of spaced-apart circular holes distributed along the longitudinal direction of the two-duct pipe 9. The inlet 11 is arranged as openings in the circumferential surface of the upstream boundary of the two-duct pipe 9 and is facing the flow direction of the fluid in the duct system 3. Furthermore the two-duct pipe 9 according to FIG. 1 is provided with an outlet 13 which is in fluid communication with said discharge duct, which outlet 13 is formed as a plurality of spaced-apart circular holes distributed along the longitudinal direction of the two-duct pipe 9. The outlet 13 is arranged as openings in the circumferential surface of the downstream boundary of the two-duct pipe 9 and is oriented in the main flow direction of the fluid in the duct system 3.

Figure 2:
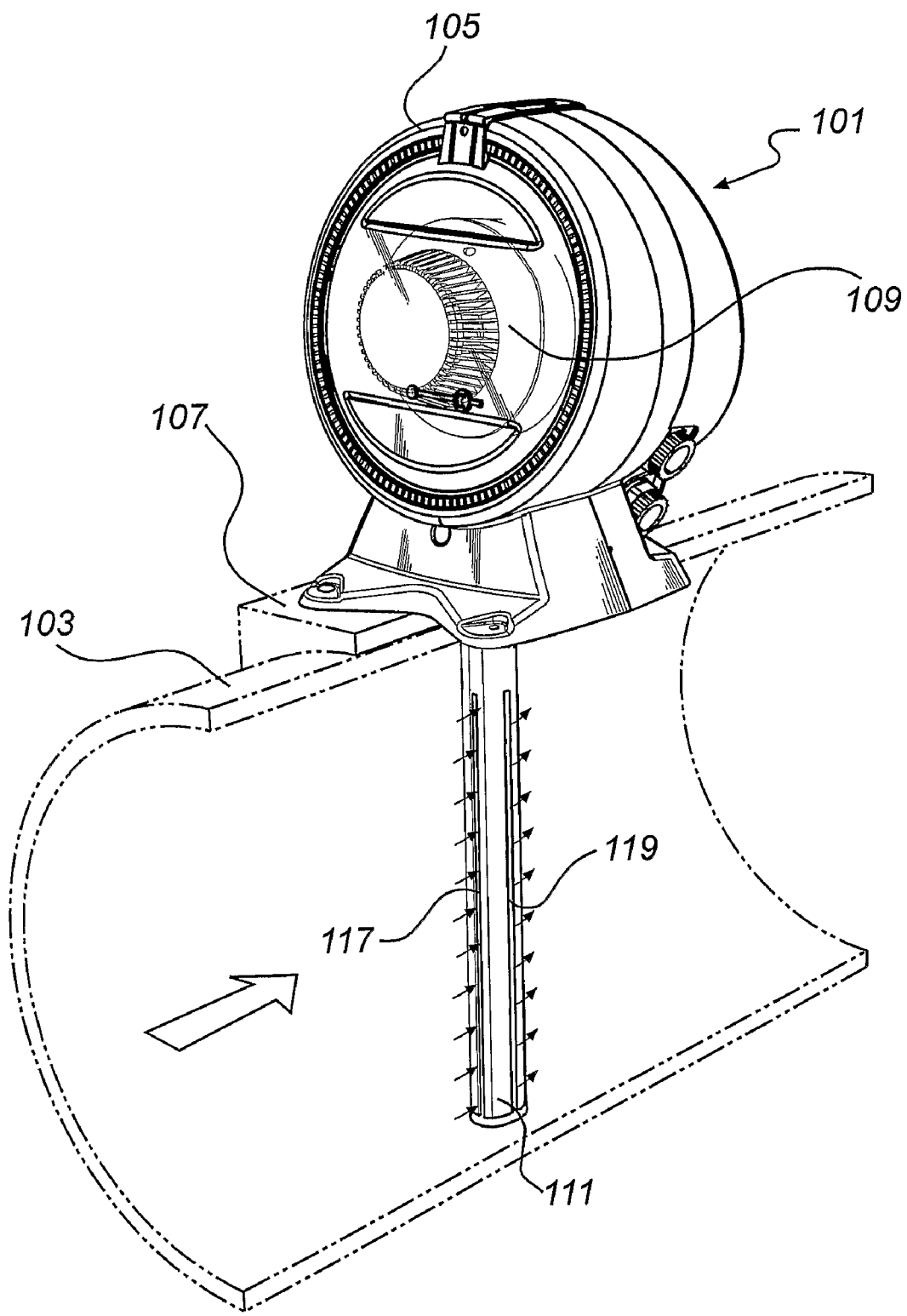
FIG. 2 schematically shows, partly in cross-section, a device according to the invention for sensing the contents of a fluid flowing in a duct system, such as in a ventilation duct.

FIG. 2 is a perspective view of a device 101 according to the invention for sensing the contents of a fluid flowing in a duct system 103, such as a ventilation duct. The device comprises a housing 105, which according to an embodiment preferably consists of a front housing element and a rear housing element which are arranged to be joined to each other. The housing 105 is adapted to be arranged on the outside of the duct system 103 containing the fluid that is to be sensed. Preferably, a fitting 107 is arranged on the outside of the duct system 103 containing the fluid that is to be sensed, the housing 105 being mounted on this fitting 107 which is positioned between the device 101 and the duct system 103.

A sensing element 109, which is known per se, is arranged inside said housing 105 to allow sensing of a fluid with a view to, for instance, identifying the presence of different kinds of particles and/or gases. Examples of such particles or gases are flue gas, carbon dioxide, oxygen, carbon monoxide, laughing gas, hydrocarbons etc. The device 101 can also be used to register, for instance, the amount of moisture in a fluid or to register the temperature of a fluid. It will be appreciated by a person skilled in the art that a device 101 according to FIG. 2 also makes it possible to simultaneously sense a plurality of the parameters stated above by way of example. Consequently the choice of the sensing element 109 which is arranged in the housing 105 essentially determines what is to be sensed.

For sensing a fluid in a duct system 103, a partial amount of the fluid in the duct at issue is diverted from the duct to a closed space of said housing 105, in which said sensing element 109 is accommodated. The partial amount of fluid is made to pass said sensing element 109 to allow identification of, for instance, particles and/or gases as described above. After sensing, the partial amount of fluid is returned to the duct. In this way, fluid is allowed to flow through a space of the housing 105 where the presence of, for instance, particles and/or gases is registered by said sensing element 109 which is arranged outside the duct system 103 inside the housing 105. For example, continuous sensing of the fluid flowing in the duct system 103 can be achieved with such a device 101 according to FIG. 2. If particles or gases are registered in the fluid from the duct system 103 by the sensing element 109, the device 101 emits, for instance, a signal which can be connected to an alarm, or which can constitute an initiation signal to close the duct system 103 etc.

The size of the partial amount of fluid that is diverted from the duct system 103 and allowed to flow through the device 101 according to FIG. 2 affects the reliability of the registration of particles and/or gases in the flowing fluid in the duct system 103. To the device 101 according to the invention as shown in FIG. 2 fluid is supplied by means of a tubular body 111 which is adapted to be inserted into the duct 103 with an extent in the transverse direction of the duct 103. The tubular body 111 suitably extends over the major part of the cross-section of the duct 103 and in particular suitably over essentially the entire cross-section of the duct 103, as shown in FIG. 2.

FIG. 3a is a perspective view of a portion of the tubular body 111 according to the invention, which tubular body 111 is intended for diversion of a partial amount of fluid from the duct system 103 to be sensed by the sensing element 109. In a preferred embodiment, the tubular body 111 is formed as a two-duct pipe with a supply duct 113 and a discharge duct 115. In a preferred embodiment according to FIG. 2, the underside of the housing 105 which is facing the duct 103 is preferably provided with a connection for receiving said tubular body 111. Thus, the tubular body 111 extends between the housing 105 and the duct 103 which contains the fluid that is to be sensed. A first portion of the housing 105 communicates with a mouth of the supply duct 113, a partial amount of fluid from the duct 103 being allowed to be supplied to the housing 105. When the partial amount of fluid supplied to the housing 105 has passed the sensing element 109, the fluid exits a mouth of the discharge duct 115 to be returned to the duct system 103. Furthermore the supply duct 113 and the discharge duct 115 are suitably closed at the end of the tubular body 111 which is facing away from the housing 105, for instance with a plug-like member or the like.

The tubular body 111 according to a preferred embodiment as shown in FIGS. 3a-3b is provided with an inlet 117 which is in fluid communication with said supply duct 113. The inlet 117 is, in use, arranged in the vicinity of the upstream boundary of the tubular body 111 so that the inlet 117 is essentially oriented towards the main flow direction of the fluid flowing in the duct 103. The orientation of the inlet 117 towards the main flow direction of the fluid in the duct 103 allows fluid to flow into the supply duct 113 of the tubular body 111 to be passed to said sensing element 109 which is arranged inside said housing 105. In use of the device 101 according to FIG. 2, the tubular body 111 extends through a peripheral surface of the wall of the duct system 103, so that the inlet 117 is positioned inside the duct system 103 and the end of the tubular body 111 which is to be joined to the housing 105 is positioned outside the duct system 103. The bushing of the tubular body 111 through the wall of the duct 103 is preferably sealed by, for instance, conventional sealing methods, such as a rubber seal which is arranged around the circumferential surface of the tubular body 111 (not shown).

In the embodiment of the tubular body 111 as shown in FIGS. 3a-3b, an outlet 119 which is in fluid communication with the discharge duct 115 is arranged upstream of the downstream boundary of the tubular body 111. It has surprisingly been found that the arrangement of the outlet 119 upstream of the downstream boundary of the tubular body 111 results in a favourable throughput of the partial amount of fluid that is diverted from the duct system 103 to be sensed by the sensing element 109 inside said housing 105. In use of the device according to FIG. 2, the outlet 119 is, similarly to the inlet 117, located inside the duct system 103 to allow the partial amount of fluid that is diverted to be sensed, to re-enter the duct 103.

The inlet 117 and the outlet 119 of the tubular body 111 have an extent which is limited inside the duct 103. Said limited extent can preferably be provided by merely arranging the inlet 117 and the outlet 119 with an extent along that part of the tubular body 117 which in use is positioned inside the duct 103. Alternatively, the inlet 117 and the outlet 119 can extend along the entire extent of the tubular body 111 between the duct 103 and the housing 105, in which case the extent of the inlet 117 and the outlet 119 along the portion of the tubular body 111 which extends between the duct 103 and the housing 105 is sealed by means of, for instance, a sleeve or the like which extends outside the circumferential surface of the tubular body 111. In a further alternative embodiment, the tubular body 111 may consist of one or more parts which are to be joined to each other, where a part of the tubular body 111 which is positioned inside the duct 103 is provided with said inlet 117 and outlet 119, respectively, and a part of the tubular body 111 which is positioned outside the duct 103 is provided with a circumferential surface without bushings.

The tubular body 111 according to FIGS. 3a-3b has a section transversely to the longitudinal direction which has a greater extent, when arranged in the duct system 103, in the main flow direction of the fluid than transversely to the main flow direction of the fluid. Moreover each side of the tubular body 111 preferably has an outer peripheral geometry with an upstream nose portion. Seen from said nose portion, along the main flow in the duct, said peripheral geometry has a relatively small radius which changes into a relatively great radius to change, in a downstream portion, via a relatively small radius to an essentially transverse extent relative to the main flow direction of the fluid. Furthermore the tubular body 111 is preferably symmetrically formed around a plane extending in the main flow direction of the fluid in the centre through the longitudinal axis of the tubular body 111.

FIG. 3b is a cross-sectional view of a particularly preferred embodiment of the tubular body 111. Said outlet 109 is in FIG. 3b arranged as opposite openings on opposite sides of the peripheral surface of the tubular body 111. In a preferred embodiment, the outlet 119 of the tubular body 111 is in FIG. 3b positioned in an area where the lateral surfaces of the tubular body 111, on opposite sides of a plane extending in the main flow direction of the fluid through the centre of the longitudinal axis of the tubular body 111, relative to each other in a direction away from said inlet 117 change from a divergent extent to a convergent extent relative to the main flow direction of the fluid. This means that the outlet 119 is preferably arranged in the area where the section of the tubular body 111 transversely to the longitudinal direction essentially has its maximum extent transversely to the main flow direction of the fluid.

It is particularly preferred to arrange the outlet 119 slightly upstream of the transition between the divergent and convergent extents of the peripheral lateral surfaces of the tubular body 111.

The invention is based on the realisation that the arrangement of the outlet 119 in the above-mentioned area results in an entraining effect through the tubular body 111 and the housing 105 which is of such a kind that an increased throughput of the partial amount of diverted fluid from the duct system 103 is allowed compared with prior art as illustrated in FIGS. 1a-b.

The tubular body 111 according to FIGS. 3a-3b is arranged with an inlet 117 and an outlet 119, which each preferably consist of at least one elongate opening extending in the longitudinal direction of the tubular body 111. Preferably said elongate opening is formed as a through slot in the peripheral circumferential surface of the tubular body 111. Measurements and analyses have demonstrated that the partial amount of fluid that is diverted from the duct system 103 comprises a more uniform distribution of fluid from the entire extent of the elongate opening transversely to the duct 103 compared with prior art where a plurality of spaced-apart circular holes are distributed along the longitudinal direction of the two-duct pipe 3 as illustrated in FIGS. 1a-1b. This realisation is based on the fact that the fluid flowing in the duct system 103 can obviously be sensed more homogeneously transversely to the duct 103 when the inlet 117 and/or outlet 119 are arranged as elongate openings, thereby allowing a more reliable and more accurate sensing of the fluid in the duct system 103. It will be appreciated by a person skilled in the art that it is also possible to arrange the inlet 117 and/or the outlet 119 as a succession of elongate openings. It will also be appreciated by a person skilled in the art that the inlet 117 and the outlet 119 can be formed in different ways relative to each other, while maintaining the effect according to the invention.

In a preferred embodiment, the tubular body 111 according to FIGS. 3a-3b has a section transversely to the longitudinal direction which has an extent in the main flow direction of the fluid which is about 30 mm and an extent transversely to the main flow direction of the fluid which is about 20 mm. Moreover, for the tubular body 111 according to FIGS. 3a-3b it is preferred to arrange the elongate openings with a width which is less than 5 mm, preferably 1-4 mm and in particular 2-3 mm.

Said tubular body 111, which comprises the supply duct 113 and the discharge duct 115, is in one embodiment preferably formed in one piece as an extruded pipe, preferably of aluminium. The inlet 117 and outlet 119 are preferably formed in connection with the extrusion of the tubular body 111, but it will be appreciated that they can also be arranged by machining the tubular body 111 after extrusion.

In one embodiment, the discharge duct 115 of the tubular body 111 is preferably arranged as two duct portions which are spaced from each other by a wall element 121. Preferably each of said duct portions is provided with an outlet 119. The wall element 121 gives the tubular body 111 advantageous stability and torsional rigidity, but it will be appreciated that according to alternative embodiments with the function maintained, it is also possible to arrange the discharge duct as one duct portion or more than two duct portions.

The invention claimed is:

1. A device for sensing the contents of a fluid flowing in a duct system, comprising:
   a sensing element; and
   a tubular body, extending over a cross-sectional portion of a duct of the duct system, including a supply conduit with an inlet facing the main flow direction of the fluid and a discharge conduit with an outlet located downstream of the inlet, to divert from the flowing fluid a partial flow which is made to pass said sensing element and then re-enter said duct, said outlet being located upstream of the downstream boundary of the tubular body, said tubular body having an outer lateral surface, the outer lateral surface having a cross-section that flares outward in the downstream direction and is approximately triangular with convex sides and rounded angles.

2. A device as claimed in claim 1, wherein the tubular body, in use, extends over the major part of the cross-section of the duct.

3. A device as claimed in claim 1, wherein the tubular body, in use, extends over essentially the entire cross-section of the duct.

4. A device as claimed in claim 1, wherein said outlet is arranged upstream of a separation point, the separation point constituting an area where the surface-parallel flow of the fluid relative to the outer lateral surface of the tubular body essentially ceases.

5. A device as claimed in claim 1, wherein said outlet is located in an area where an essentially maximum speed of the surface-parallel flow relative to the outer lateral surface of the tubular body occurs.

6. A device as claimed in claim 1, wherein said outlet is located in an area where the lateral surfaces of the tubular body relative to each other, in a direction away from said inlet, change from a divergent extent to a convergent extent relative to the main flow direction of the fluid.

7. A device as claimed in claim 1, wherein at least one of the inlet and outlet includes at least one elongate opening.

8. A device as claimed in claim 7, wherein said elongate opening has a width which is less than 5 mm.

9. A device as claimed in claim 7, wherein said elongate opening extends along the major part of the portion of the tubular body which in use is positioned inside said duct.

10. A device as claimed in claim 7, wherein said elongate opening includes a plurality of elongate openings which are spaced from each other in the longitudinal direction of the tubular body.

11. A device as claimed in claim 7, wherein the least one elongate opening is a slot.

12. A device as claimed in claim 1, wherein a section of the tubular body transversely to the longitudinal direction has a greater extent in the main flow direction of the fluid than transversely to the main flow direction of the fluid.

13. A device as claimed in claim 1, wherein said outlet includes at least two opposite openings positioned on opposite sides of the tubular body relative to the main flow direction of the fluid.

14. A device as claimed in claim 1, wherein said discharge conduit includes two duct portions which are spaced apart by a wall element, each duct portion being provided with an outlet.

15. A device as claimed in claim 1, wherein the duct system includes a ventilation duct.

16. The device of claim 1, wherein the outer lateral surface has a radius of curvature that increases between the inlet and the outlet.

17. The device of claim 1, wherein, the tubular body has a cross-sectional width that is orthogonal to the main direction of the fluid, the outlet being located on the tubular body at a location where the cross-sectional width is maximized.

* * * * *